US00PP32352P2

(12) United States Plant Patent
Wood

(10) Patent No.: US PP32,352 P2
(45) Date of Patent: Oct. 20, 2020

(54) ***CONTINUS* PLANT NAMED 'SMNCCPP3'**

(50) Latin Name: *Cotinus coggygria*
Varietal Denomination: SMNCCPP3

(71) Applicant: Timothy D. Wood, Spring Lake, MI (US)

(72) Inventor: Timothy D. Wood, Spring Lake, MI (US)

(73) Assignee: Spring Meadow Nursery Inc., Grand Haven, MI (US)

( * ) Notice: Subject to any disclaimer, the term of this patent is extended or adjusted under 35 U.S.C. 154(b) by 0 days.

(21) Appl. No.: 16/602,684

(22) Filed: Nov. 18, 2019

(51) Int. Cl.
*A01H 5/02* (2018.01)

(52) U.S. Cl.
USPC ..... Plt./226

(58) Field of Classification Search
USPC ..... Plt./226
CPC ..... A01H 5/02
See application file for complete search history.

*Primary Examiner* — Annette H Para
(74) *Attorney, Agent, or Firm* — C. A. Whealy

(57) ABSTRACT

A new and distinct cultivar of *Cotinus* plant named 'SMNCCPP3', characterized by its upright and outwardly spreading plant habit; freely branching habit; dense and bushy appearance; leaves that are initially greyed purple in color becoming dark green with development; freely flowering habit; inflorescences with numerous light greyed purple-colored pedicel hairs; and good garden performance.

2 Drawing Sheets

Figure 1:
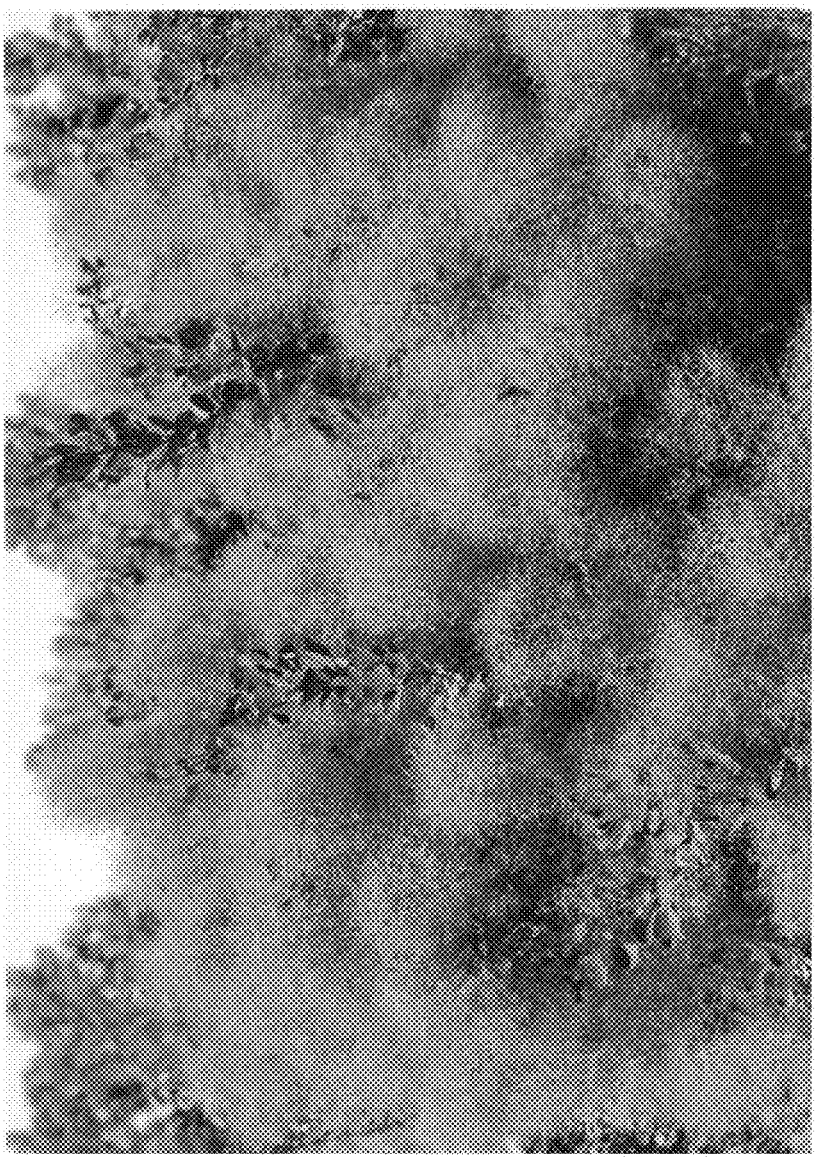

Botanical designation: *Cotinus coggygria.*
Cultivar denomination: 'SMNCCPP3'.

BACKGROUND OF THE INVENTION

The present invention relates to a new and distinct *Cotinus* plant, botanically known as *Cotinus coggygria* and hereinafter referred to by the name 'SMNCCPP3'.

The new *Cotinus* plant is a product of a planned breeding program conducted by the Inventor in Grand Haven, Mich. The objective of the breeding program was to create new *Cotinus* plants with strong branches and attractive plant form and flower coloration.

The new *Cotinus* plant originated from an open-pollination during the summer of 2011 in Grand Haven, Mich. of *Cotinus coggygria* 'Little Ruby', not patented, as the female, or seed, parent with an unknown selection of *Cotinus coggygria* as the male, or pollen, parent. The new *Cotinus* plant was discovered and selected by the Inventor as a single flowering plant within the progeny of the stated open-pollination in a controlled environment in Grand Haven, Mich. during the spring of 2013.

Asexual reproduction of the new *Cotinus* plant by softwood stem cuttings in a controlled environment in Grand Haven, Mich. since the spring of 2013 has shown that the unique features of this new *Cotinus* plant are stable and reproduced true to type in successive generations.

SUMMARY OF THE INVENTION

Plants of the new *Cotinus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'SMNCCPP3'. These characteristics in combination distinguish 'SMNCCPP3' as a new and distinct *Cotinus* plant:

1. Upright and outwardly spreading plant habit.
2. Freely branching habit; dense and bushy appearance.
3. Leaves that are initially greyed purple in color becoming dark green with development.
4. Freely flowering habit.
5. Inflorescences with numerous light greyed purple-colored pedicel hairs.
6. Good garden performance.

Plants of the new *Cotinus* differ primarily from plants of the female parent, 'Little Ruby', in plant size as plants of the *Cotinus* are larger than plants of 'Little Ruby'. In addition, plants of 'Little Ruby' have more reddish-colored developing leaves than plants of the new *Cotinus.*

Plants of the new *Cotinus* can be compared to plants of *Cotinus coggygria* 'Royal Purple', not patented. In side-by-side comparisons, plants of the new *Cotinus* differ primarily from plants of 'Royal Purple' in plant form as plants of the new *Cotinus* are more shrub-like whereas plants of 'Royal Purple' are more tree-like. In addition, plants of 'Royal Purple' have more maroon-colored developing leaves than plants of the new *Cotinus.*

BRIEF DESCRIPTION OF THE PHOTOGRAPHS

The accompanying colored photographs illustrate the overall appearance of the new *Cotinus* plant showing the colors as true as it is reasonably possible to obtain in colored reproductions of this type. Colors in the photographs may differ slightly from the color values cited in the detailed botanical description which accurately describe the colors of the new *Cotinus* plant.

The photograph on the first sheet (FIG. 1 of 2) is a side perspective view of a typical flowering plant of 'SMNCCPP3' grown in an outdoor nursery.

Figure 2:
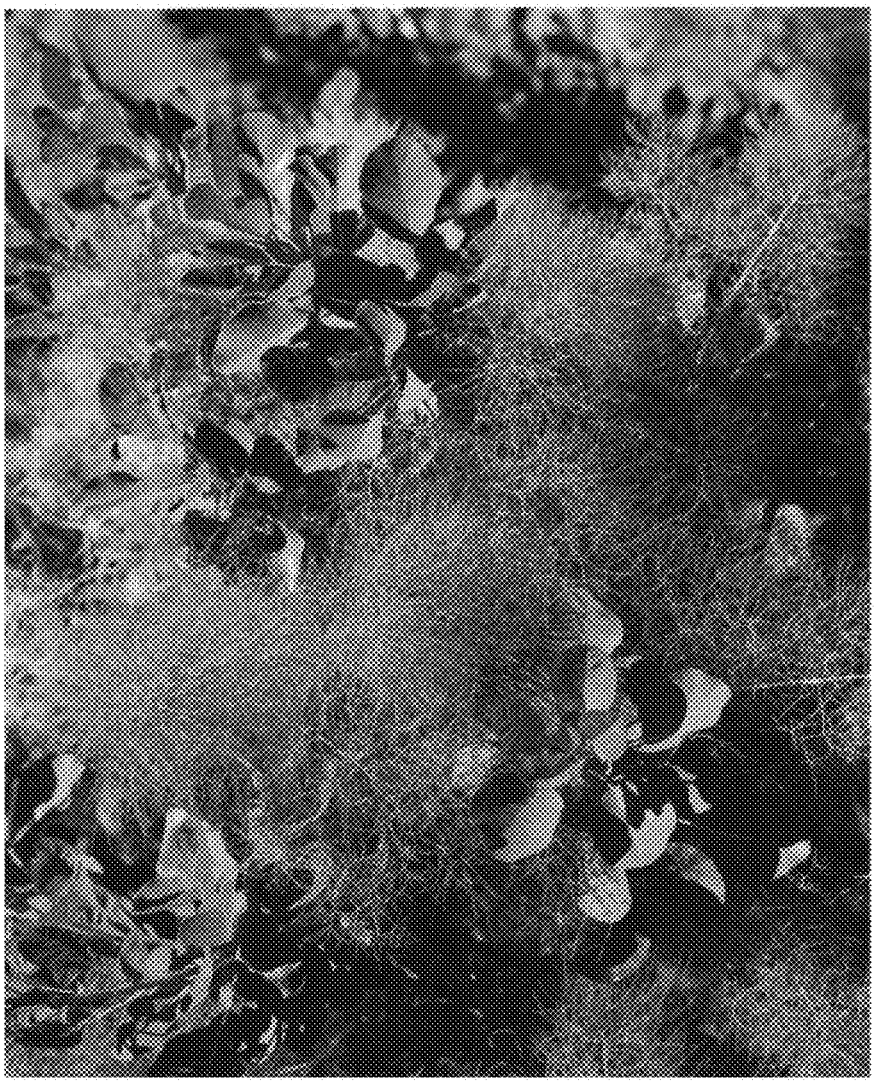

The photograph on the second sheet (FIG. 2 of 2) is a close-up view of typical leaves and inflorescences of a plant of 'SMNCCPP3'.

DETAILED BOTANICAL DESCRIPTION

The aforementioned photographs and following observations, measurements and values describe plants grown during the spring and summer in three-gallon containers in polyethylene-covered greenhouses in Grand Haven, Mich. and under cultural practices typical of commercial *Cotinus* production. Plants were five years old when the photographs were taken and two years old when the description was taken. During the production of the plants, day temperatures ranged from 18° C. to 27° C. and night temperatures ranged from 5° C. to 10° C. In the following description, color references are made to The Royal Horticultural Society Colour Chart, 2015 Edition, except where general terms of ordinary dictionary significance are used.

Botanical classification: *Cotinus coggygria* 'SMNCCPP3'.

Parentage:

*Female, or seed, parent.*—*Cotinus coggygria* 'Little Ruby', not patented.

*Male, or pollen, parent.*—Unknown selection of *Cotinus coggygria*, not patented.

Propagation:

*Type.*—By softwood stem cuttings.

*Time to initiate roots plant, summer.*—About six weeks at temperatures ranging from 18° C. to 27° C.

*Time to produce a rooted plant, summer.*—About twelve weeks at temperatures ranging from 18° C. to 27° C.

*Root description.*—Medium in thickness, fibrous; typically white in color, actual color of the roots is dependent on substrate composition, water quality, fertilizer, substrate temperature and physiological age of roots.

*Rooting habit.*—Freely branching; dense.

Plant description:

*Plant and growth habit.*—Deciduous perennial shrub; upright and outwardly spreading plant habit; relatively short internodes; dense and bushy appearance; moderately vigorous growth habit and moderate growth rate.

*Plant height.*—About 44 cm.

*Plant width (spread).*—About 61 cm.

*Lateral branches.*—Quantity: Freely branching habit with about 25 primary lateral branches developing per plant. Length: About 32 cm. Diameter: About 3 mm. Internode length: About 1.5 cm. Strength: Strong. Aspect: Erect to about 45° from vertical. Texture: Smooth, glabrous. Color, developing: Close to 187A. Color, developed: Close to 198A.

Leaf description:

*Arrangement and appearance.*—Opposite, simple.

*Length.*—About 4 cm.

*Width.*—About 2.9 cm.

*Shape.*—Orbicular to elliptic.

*Apex.*—Obtuse.

*Base.*—Attenuate.

*Margin.*—Slightly crenate.

*Texture, upper surface.*—Smooth, glabrous.

*Texture, lower surface.*—Venation prominent.

*Venation pattern.*—Pinnate.

*Color.*—Developing leaves, upper surface: Close to N186C and 143A. Developing leaves, lower surface: Close to 147C and 187B. Fully expanded leaves, upper surface: Close to 147A; venation, close to between 184D and 185C. Fully expanded leaves, lower surface: Close to 191A; venation, close to 185C and with development, close to 145D.

*Petioles.*—Length: About 2.7 cm. Diameter: About 1 mm. Texture, upper and lower surfaces: Smooth, glabrous. Color, upper surface: Close to 152D. Color, lower surface: Close to 150C.

Flower description:

*Flower type and flowering habit.*—Single flowers arranged on terminal panicles; inflorescences face mostly upright to outwardly; freely flowering habit with more than 100 flowers developing per inflorescence; flowers face upright to outwardly depending on position on the panicle; flowers not persistent; numerous pedicel hairs giving a "smoky" appearance to the inflorescences.

*Fragrance.*—None detected.

*Natural flowering season.*—Plants flower continuously during May and June in Michigan.

*Flower buds.*—Height: About 1.5 cm. Diameter: About 1 mm. Shape: Oblong. Color: Close to 187A.

*Inflorescence length.*—About 17 cm.

*Inflorescence diameter.*—About 16 cm.

*Flower diameter.*—About 2 mm.

*Petals.*—Quantity per flower: Typically five in a single whorl; inconspicuous. Length: About 1 mm. Width: About 1 mm. Shape: Ovate. Apex: Acute. Base: Cuneate. Margin: Entire. Texture, upper and lower surfaces: Smooth, glabrous. Color, upper and lower surfaces: Close to 185D.

*Sepals.*—Quantity per flower: Typically five in a single whorl; inconspicuous. Length: About 1 mm. Width: About 1 mm. Shape: Ovate. Apex: Acute. Base: Cuneate. Margin: Entire. Texture, upper and lower surfaces: Smooth, glabrous. Color, upper and lower surfaces: Close to 144C.

*Peduncles.*—Length: About 15.8 cm. Diameter: About 2 mm. Strength: Moderately strong. Angle: Upright to outwardly. Texture: Smooth, glabrous. Color: Close to 187A.

*Pedicels.*—Length: About 6 mm. Diameter: Less than 1 mm. Strength: Moderately strong. Texture: Long dense and showy pubescence; about 8 mm in length and close to 187A in color. Color: Close to 187A.

*Reproductive organs.*—Stamens: Quantity per flower: Typically five. Filament length: About 1 mm. Filament color: Close to 144B. Anther length: Less than 1 mm. Anther shape: Reniform. Anther color: Close to 15A. Pollen amount: Scarce. Pollen color: Close to 15A. Pistils: Quantity per flower: One. Pistil length: Less than 1 mm. Stigma shape: Club-shaped. Stigma color: Close to 144B. Style length: Less than 1 mm. Style color: Close to 144B. Ovary color: Close to 144B.

*Seeds and fruits.*—To date, seed and fruit development have not been observed on plants of the new *Cotinus*.

Pathogen & pest resistance: To date, plants of the new *Cotinus* have not been observed to be resistant to pathogens and pests common to *Cotinus* plants.

Garden performance: Plants of the new *Cotinus* have been observed to have good garden performance and tolerate rain, wind and to tolerate temperatures ranging from about −32° C. to about 36° C.

It is claimed:

1. A new and distinct *Cotinus* plant named 'SMNCCPP3' as illustrated and described.

* * * * *